United States Patent
Farley et al.

[11] Patent Number: 5,984,865
[45] Date of Patent: Nov. 16, 1999

[54] SURGICAL RETRACTOR HAVING LOCKING INTERCHANGEABLE BLADES

[75] Inventors: Daniel K. Farley, Traverse City; Anthony J. Mulac, East Jordan, both of Mich.

[73] Assignee: Thompson Surgical Instruments, Inc., Traverse, Mich.

[21] Appl. No.: 09/153,633

[22] Filed: Sep. 15, 1998

[51] Int. Cl.⁶ .................................................. A61B 17/00
[52] U.S. Cl. ............................................................ 600/213
[58] Field of Search ................................ 600/201, 213, 600/215, 226

[56] References Cited

U.S. PATENT DOCUMENTS

| | | |
|---|---|---|
| 1,660,989 | 1/1928 | Carpenter . |
| 2,693,795 | 11/1954 | Grieshaber . |
| 3,749,088 | 7/1973 | Kohlmann . |
| 3,965,890 | 6/1976 | Gauthier . |
| 4,010,741 | 3/1977 | Gauthier . |
| 4,211,127 | 7/1980 | D'Oporto et al. ........................... 81/63 |
| 4,399,722 | 8/1983 | Sardo, Jr. ..................................... 81/60 |
| 4,420,995 | 12/1983 | Roberts ....................................... 81/60 |
| 4,865,485 | 9/1989 | Finnefrock, Sr. ....................... 403/322 |
| 4,896,661 | 1/1990 | Bogert et al. ............................. 606/86 |
| 4,934,352 | 6/1990 | Sullivan, Jr. . |
| 5,037,299 | 8/1991 | Nakanishi ............................... 433/128 |
| 5,381,788 | 1/1995 | Matula et al. . |

Primary Examiner—Jeffrey A. Smith
Attorney, Agent, or Firm—McAndrews, Held & Malloy, Ltd.

[57] ABSTRACT

A surgical retractor is provided including a handle, a blade, and a head member with a locking mechanism for locking the blade within the head member. The locking mechanism includes a plunger and spring combination that is actuable to receive and release the blade from the head member.

18 Claims, 3 Drawing Sheets

U.S. Patent    Nov. 16, 1999    Sheet 1 of 3    5,984,865
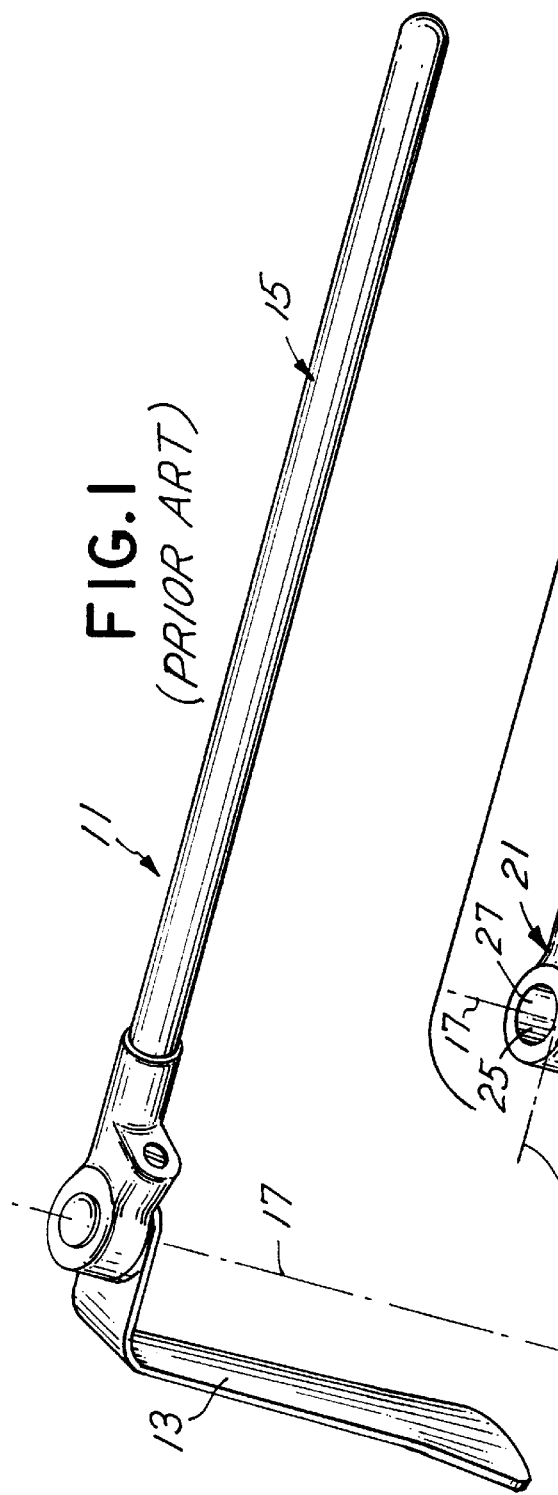
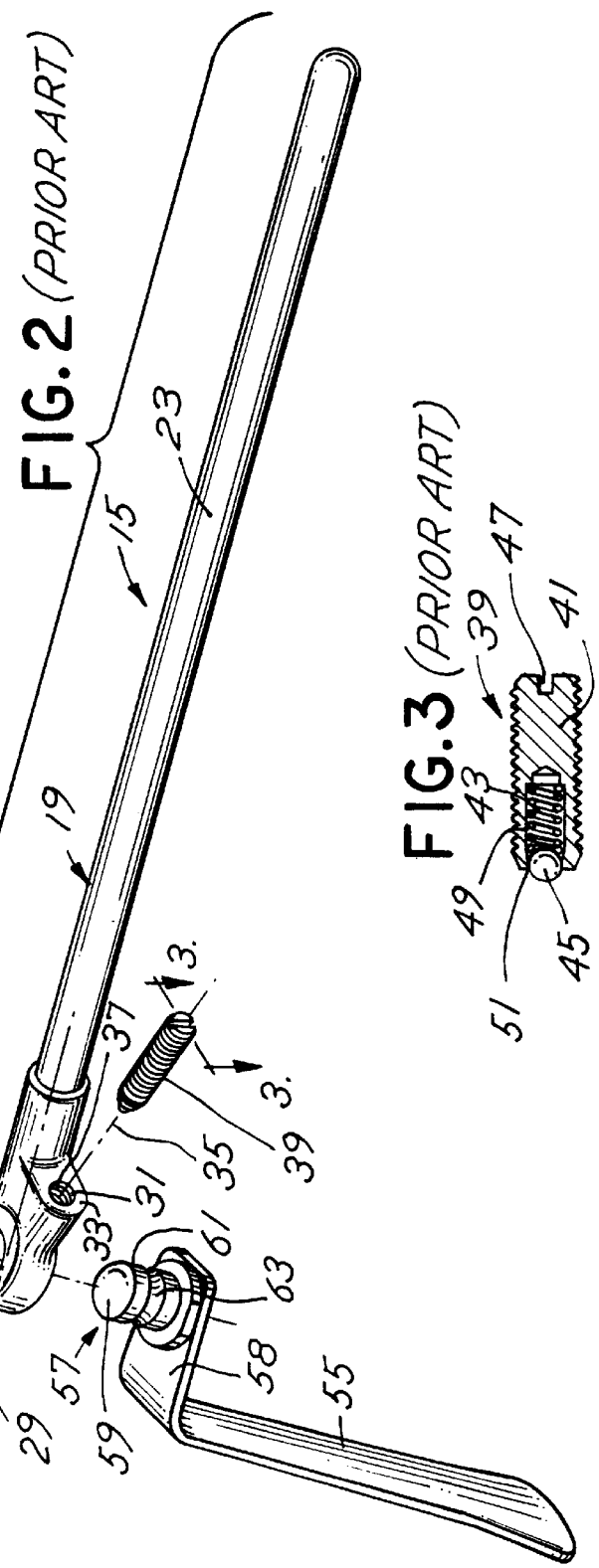
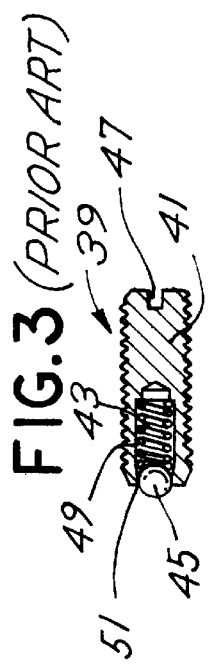

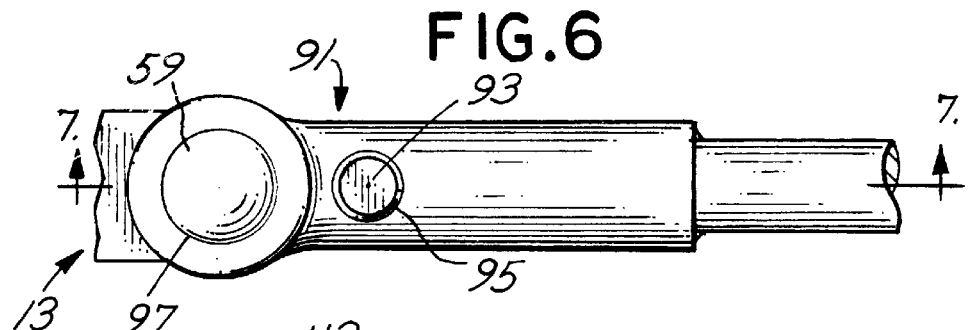
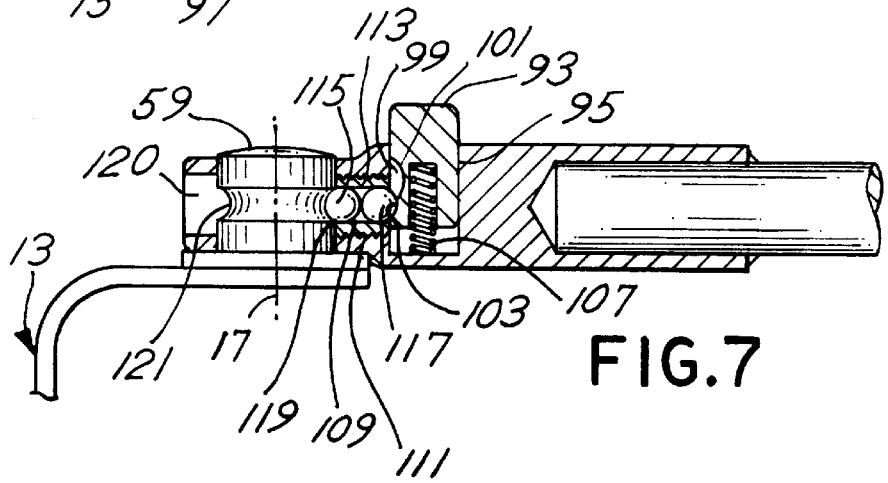
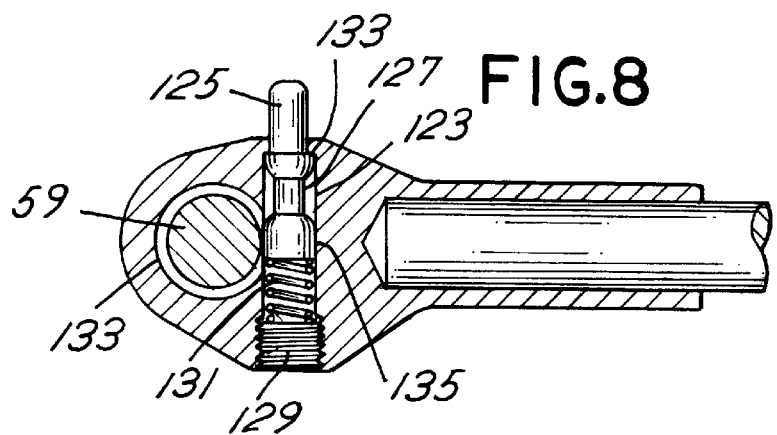
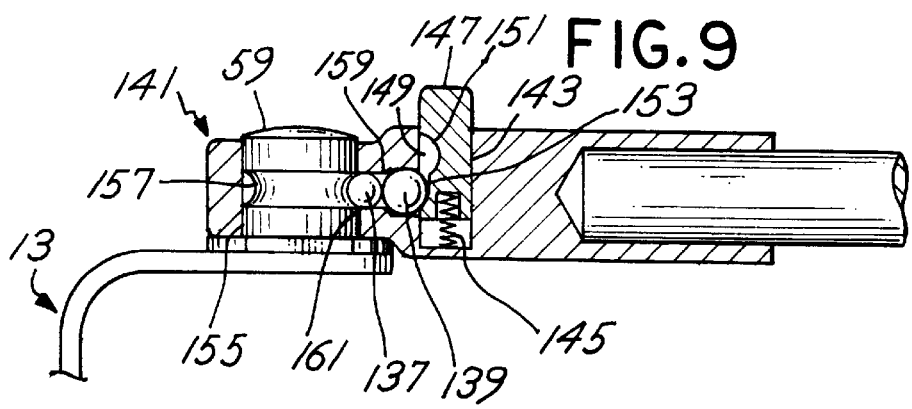

SURGICAL RETRACTOR HAVING LOCKING INTERCHANGEABLE BLADES

BACKGROUND OF THE INVENTION

The invention relates to surgical retractors used in abdominal, thoracic and cardiac surgery, to properly retain the tissues surrounding the surgical incision, and more particularly relates to a retractor having a rotatable blade which is quickly and easily replaced by another blade.

In abdominal surgery, it is particularly important that the patient's abdominal region be well exposed to facilitate work by the surgeon. To effect this desired exposure, several surgical retractors are normally employed which engage and hold the skin apart at the incision during the course of the operation.

Most retractors comprise a handle connected to a blade. The blade can be of a variety of constructions including, for example, a paddle-like design or a finger-like configuration. The type of retractor blade used depends on a number of factors including, the size of the incision, the size of the patient and the type of surgery to be performed.

Oftentimes, a surgeon is required to change the type of retractor blade being used, during the course of an operation. To this end, a variety of interchangeable retractor blade systems have been proposed which allow for the blade to be released from the retractor handle whereby one blade can be removed and another put in its place. This type of arrangement allows a single retractor handle to be used with a variety of blades.

Some of the drawbacks of the interchangeable blade retractor of the prior art includes limited movement of the blade relative to the retractor handle, and the tendency of the blade to spontaneously disconnect from the handle during surgery.

Therefore, it is an object of the present invention to provide an interchangeable retractor blade system wherein the retractor blade is locked firmly to the retractor handle and cannot be removed without positive action of the physician or other operating room personnel.

It is another object of the present invention to provide an interchangeable retractor blade system wherein the retractor blade is fully rotatable about its vertical axis when engaged with the retractor handle.

BRIEF SUMMARY OF THE INVENTION

These and other objects of the invention are achieved in a surgical retractor comprised of a handle and a blade. The blade is releasably held to the handle by a locking member which frictionally retains the blade from vertical movement to prevent blade release without applied force while permitting rotational movement relative to the vertical.

BRIEF DESCRIPTION OF THE DRAWINGS

FIG. 1 is a perspective view of a surgical retractor of the prior art.

FIG. 2 is an exploded view of the retractor of FIG. 1 revealing the handle and blade and the screw member.

FIG. 3 is a cross-sectional side view of the screw member of FIG. 2.

FIG. 6 is a partial top view of a second embodiment of a latch-mechanism retractor.

FIG. 7 is a partial cross-sectional side view of the latch-mechanism of FIG. 6.

FIG. 8 is a partial cross-sectional top view of a third embodiment of a latch-mechanism for use in a retractor.

FIG. 9 is a partial cross-sectional side view of a fourth embodiment of a latch-mechanism for use in a retractor.

DETAILED DESCRIPTION OF THE PREFERRED EMBODIMENT

Figure 4:
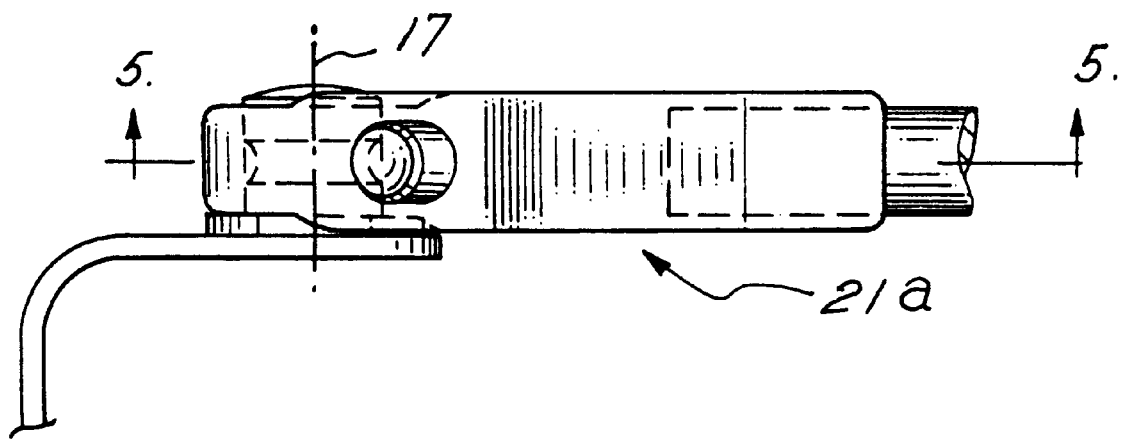
FIG. 4 is a partial side view of a surgical retractor according to the present invention.

Referring to FIGS. 1 and 2, a retractor 11 includes a blade member 13 and a handle 15. Blade member 13 is rotatably mounted to handle 15 providing a 360 degree rotational movement of the blade member 13 about an axis 17. Blade member 13 is constructed for making contact with the incised skin of the patient to pull and hold the skin back to expose a surgical site. As understood, handle 15 is held by a retractor system (not shown), which is securely positioned relative to the patient. The handle 15 is clamped in place relative to the system, but thereafter may be moved and reclamped at another location by the physician or other operating room personnel. The operator thus secures the handle at various locations relative to the incision and may adjust the position of the handle during the surgery.

Referring to FIG. 2, handle 15 includes an elongated cylindrical shaft 19 and a head member 21. Shaft 19 includes an outer cylindrical surface 23 against which a clamp (not shown) may be tightened to secure the retractor 11 relative to the system and thus relative to the incision. Head member 21 is fixed at one end of shaft 19 and may be welded or otherwise secured thereto.

Referring to FIGS. 2 and 3, head member 21 includes an opening 25 defined by a cylindrical surface 27 passing entirely through the head member 21. Opening 25 has a cylindrical axis 17 disposed at right angles to the axis 29 of cylindrical shaft 19. The prior art device that is shown includes a second opening or aperture 31 that is also formed in head member 21 and is disposed laterally to opening 25. Aperture 31 intersects opening 25 communicating opening 25 to the outer surface 33 of member 21. Aperture 31 has a cylindrical axis 35 disposed perpendicular to, and intersecting, axis 17 of opening 25. Axis 35 is disposed at an acute angle to axis 29 of the shaft.

Figure 5:
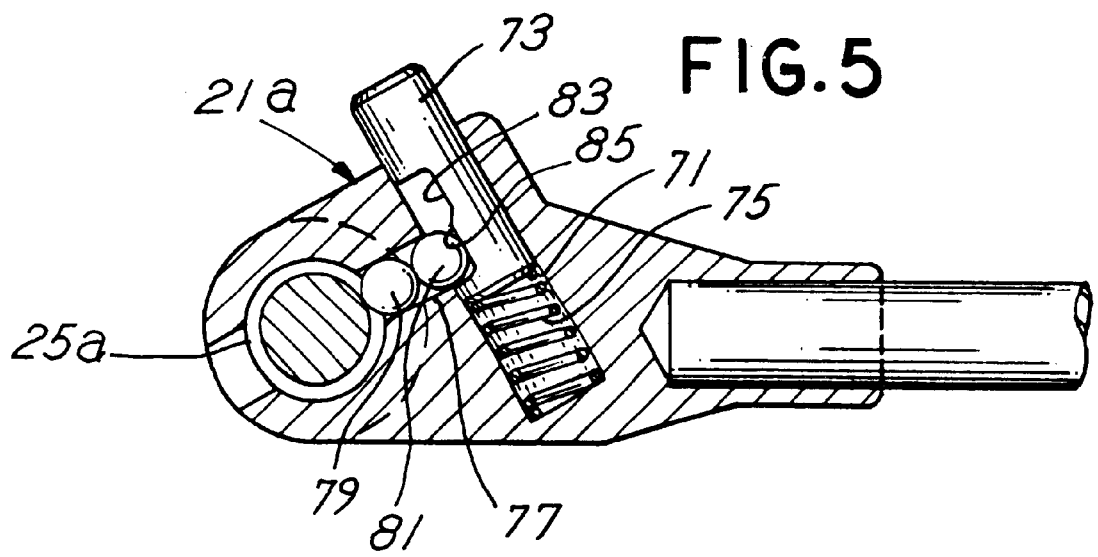
FIG. 5 is a partial cross-sectional top view of a latch-mechanism for use in the retractor of FIG. 4.

Aperture 31 has its defining wall threaded at 37 for threadingly receiving a screw member 39. Screw member 39 includes a body member 41, a spring 43 and a ball bearing 45. The distal end of body member 41 includes a slot 47 of a size to receive a screw driver blade for screwing body member 41 into aperture 31. The body member 41 is screwed into the aperture so that ball 45 is permitted to extend a small distance into opening 25, as shown in FIG. 5.

As shown in FIG. 3, body member 41 includes a hollow chamber 49 within which is housed spring 43 and ball 45. The proximal end of chamber 49 is smaller in diameter than ball 45 providing an annular stop surface 51 against which ball 45 rests. Ball 45 is sized to permit axial movement of the ball along the walls of chamber 49.

Spring 43 is compressed within the chamber and biases ball 45 to its fullest extent against stop surface 51. Body member 39 is turned into the aperture 31 to a point where ball 45 is disposed just inside of surface 27 of the head member 21.

Referring again to FIG. 2, blade member 13 is constructed from a blade 55 and a connector head 57. Blade 55 may be shaped as a paddle with a curved or contour surface for contacting the surgery patient at a surgical incision. Connector head 57 is connected at one end of blade 55 and is integrally formed thereto. Connector head 57 includes a flat member 58 extending outwardly from the surface of the blade paddle 55 and an axle member 59. Axle member 59 provides an outer bearing surface 61 which bears against surface 27, of aperture 25. Axle member 59 includes a grooved annular area 63 which mates with the ball 45 of screw member 39. Ball 45 is spherical so that contact with axle member 59 as the member 59 is forced up into aperture 25 forces the ball 45 into chamber 49 away from aperture 25 and against spring 43. The ball remains fully within aperture 31 until groove 63 aligns with the ball allowing the ball to move back into the aperture 25. The ball frictionally engages axle member 59 into head member 21. The frictional engagement is sufficient to retain the blade 13 to the handle 15, while permitting blade 13 to be rotated and to be easily removed from the handle by pulling the blade with some force in the direction of axis 17.

This locking mechanism of the prior art described above has been widely used because it provides the beneficial features of a completely rotatable blade that is removable for replacement. This prior art configuration, however, is also prone to unintended and unexpected release of the blade during surgical procedures.

Referring to FIGS. 4 and 5, a first embodiment of an attachment mechanism of the present invention is shown. The present invention utilizes a handle 15 and a blade member 13 identical to those of the prior art. The head member 21a, however, includes a new locking configuration that provides the retractor of the present invention with a more secure structure for retaining the blade member 13. It is also intended that the blade members 13 that are compatible with the prior art device of FIGS. 1–3 will also be compatible with the configuration of the present invention. In this way, surgeons presently using the prior art system described above can utilize the blade members in the combination of the present invention. The head member 21a includes a cylindrical channel 71 formed in head member 21a. Channel 71 does not pass clear through the head member 21a and is disposed orthogonal to axis 17 but without intersecting axis 17.

A plunger 73 and spring 75 are disposed in channel 71. In its unbiased state (shown in FIG. 5), spring 75 retains plunger 73 in the position shown. Plunger 73 is of a length so that a portion protrudes from head member 21a as shown. The operator of the retractor may use his or her thumb to press plunger 73 into channel 71 against the force of spring 75.

A second cylindrical channel 77 is disposed between and connects aperture 25a and first channel 71. A pair of steel ball bearings 79, 81 are housed in second channel 77. The proximal end of channel 77 where the channel meets opening 25a included an annular stop to prevent ball 79 from moving completely into opening 25a. Only a portion of ball 79 may move into opening 25a.

Plunger 73 includes two separate grooves 83, 85 which receive ball 81. When groove 85 engages ball 81, ball 81 is forced against ball 79 driving ball 79 into its fullest extent into opening 25a. When groove 83 engages ball 81, both balls have a larger area so that ball 79 may move fully out of channel 25a.

The pressing of plunger 73 against spring 75 moves groove 83 into a position to receive ball 81. This removes the force of ball 79 against the axle member 59 of the connector head allowing the blade to be removed. A different blade may then be inserted into opening 25a while the plunger is depressed. When the plunger is next released, the ball 79 is forced against the axle member frictionally retaining the axle member to head member 21 a while allowing rotation of the blade.

It should be understood that ball bearings 79, 81 can be replaced with balls that are not spherical and that even have angled edges so long as the balls that are used are slidably housed within the second channel 77 such that they can be made to engage and withdraw from aperture 25 as described above. It should be further understood that the two ball bearings 79, 81 can be replaced by a single ball that need not be spherical.

The attachment mechanism of the present invention is preferably constructed as follows. The head member 21a is provided with the opening 25a and the two channels 71, 77. The spring 75 is first inserted into the first channel 71. The plunger is next inserted into first channel 71 and depressed to compress spring 75 and to align groove 83 with the second channel 77. Balls 79, 81 may then be inserted into second channel 77 through the access at opening 25a. As the groove 83 of plunger 73 is aligned with second channel 77, ball 88 will be able to move through second channel 77 into groove 83 so that ball 79 can be positioned entirely within second channel 77 and not at all in opening 25. While still depressing plunger 73 into first channel 71, the access from second channel 77 to opening 25 is peened to a diameter smaller than ball 79. In this way when plunger 73 is released, balls 79, 81 are biased toward opening 25a but are prevented from exiting second channel 77. Only a portion of ball 79 is permitted to extend into opening 25a. The portion of ball 79 that extends into opening 25a when the plunger 73 is not depressed will engage groove 63 (FIG. 2) of the connector head 57 of blade member 13.

FIGS. 6 and 7 show a second embodiment of an attachment mechanism. As shown in FIG. 6, head member 91 includes a plunger 93 inserted into a channel 95 that is parallel to axis 17. Axle member 59 of blade 13 can be seen within opening 97 of head member 91.

FIG. 7 is a partial cross-sectional side view of the latch-mechanism of FIG. 6. Plunger 93 is formed with a groove 99 having a deeper portion 101 and a shallow portion 103. Plunger 93 is also provided with an internal cavity to house spring 107. Plunger 93 is provided with this internal cavity 104 to permit the housing of a spring 107 with sufficient strength to bias plunger 93 away from channel 95.

Head member 91 is also provided with a second channel 109. This second channel has a threaded inner bore 111 that is intended to receive a threaded member 113. Threaded member 113 houses stainless steel ball bearings 115 and 117. Threaded member 113 and its ball bearings 115, 117 can be threaded into position through an opening 120 that is located at the distal end of head member 91 and provides access to opening 97 and second channel 109.

Threaded member 113 should be threaded into threaded inner bore 111 such that it does not protrude into opening 97. Instead, only a portion of ball bearing 115 protrudes into opening 97. Ball bearing 117 is positioned to cooperate with groove 99. Specifically, when plunger 93 is not depressed into channel 95 shallow portion 103 of groove 99 contacts ball bearing 117 and urges it toward opening 97 thereby also urging ball bearing 115 such that a portion of ball bearing 115 extends into opening 97. Of course, threaded member 113 should be provided with an end diameter 119 that is smaller than the diameter of ball 115 but that permits a portion of ball bearing 115 to extend into opening 97.

As shown in FIG. 7, such a configuration permits ball bearing 115 to engage groove 121 of axle member 59. When plunger 93 is depressed into channel 95, deeper portion 101 of groove 99 aligns with second channel 109 permitting ball bearing 117 to partially exit second channel 109 and thereby permitting ball bearing 115 to withdraw from opening 97 entirely and reside within second channel 109. This frees axle member 59 from its locked configuration and permits a user to remove blade member 13 from head member 91.

FIG. 8 shows a third embodiment of an attachment mechanism wherein a channel 123 passes completely through the head member. A plunger 125 has a grooved area 127 which is positionable relative to axle member 59 for releasing the axle member. A threaded screw 129 retains spring 131 and plunger 125 in position so that spring 131 forces plunger 125 against a stop member 133 formed as an annular restriction in the channel 123.

As is evident from FIG. 8, axle member 59 is retained within opening 133 when the plunger 125 is in its normal position (i.e., when it is not depressed into channel 123) and bead 135 of plunger 125 is permitted to engage the groove (not shown) of axle member 59. To provide the head member of FIG. 8 with the locking characteristics of the present invention, channel 123 must be tangential to opening 133 such that a portion of bead 135 can protrude into opening 133 when plunger 125 is in its normal position. Only when plunger 125 is depressed into channel 123 and grooved area 127 aligns with the access from channel 123 to opening 133, will axle member 59 be free from engagement with the plunger 125 and removable from opening 133

FIG. 9 shows a fourth embodiment of an attachment mechanism similar to the embodiment of FIG. 7. In the embodiment of FIG. 9, however, a small ball bearing 137 and a large ball bearing 139 are used in second channel 159 in place of two ball bearings of equal diameter. Specifically, head member 141 is provided with a channel 143 into which a spring 145 and a plunger 147 may be inserted. The plunger 147 has a groove 149 with a deeper portion 151 and a shallow portion 153. Axle member 59 is retained within opening 155 when small ball bearing 137 engages groove 157. To remove axle member 59 from opening 155, the plunger 147 must be depressed into channel 143 such that the deeper portion 151 of groove 149 aligns with second channel 159 so that large ball bearing 139 can cooperate with deeper portion 151 of plunger 147 to permit small ball bearing 137 to withdraw from the opening 155 and the groove 157 of axle member 59. Second channel 159 will also be provided with a diameter at its distal end 161 that is smaller than the diameter of small ball bearing 137. In this way, small ball bearing 137 will be permanently retained within second channel 159.

The attachment mechanism of head member 141 can be constructed by first providing the head member with the opening 155, the channel 143 and second channel 159. A large ball bearing 139 can then be inserted into the channel 143 and into the second channel 159. The spring 145 and plunger can then be inserted into the channel 143. Plunger 147 can be depressed into channel 143 such that the deeper portion 151 of groove 149 aligns with the second channel 159. This alignment enables the large ball bearing 139 to sit within the deeper portion 151 of the groove 149. A small ball bearing 137 can then be inserted into the second channel 159 through the opening 155. Because the plunger 147 is in its depressed position and the large ball bearing 139 is engaged in the deeper portion 151 of the groove 149, the small ball bearing 137 will be able to be completely housed within the second channel 159. At this time, while the plunger 147 is still depressed, the axis from the second channel 159 to the opening 155 is peened to a diameter smaller than the diameter of the small ball bearing 137.

While the invention has been particularly shown and described with reference to preferred embodiments thereof, it will be understood by those skilled in the art that various modifications in form and detail may be made therein without departing from the scope and spirit of the invention. Accordingly, modifications such as those suggested above, but not limited thereto are to be considered within the scope of the invention.

We claim:

1. A surgical retractor comprising a handle and a blade member, the blade member interlocking with the handle and rotatably mounted thereto, the handle including:
   (i) a head member having an aperture defined by a cylindrical surface; and
   (ii) a lock for securing the blade member to the handle whereby the blade member when secured is rotatable about an axis passing through the center of the aperture, the lock including a biased plunger,
the blade member comprising
   (i) a blade; and
   (ii) a connector secured to the blade and sized for moving within the aperture, the connector having an outer cylindrical surface of a size for bearing against the inner cylindrical surface during rotation of the blade member relative to the handle, the lock engaging the connector when the connector is moved into the aperture for securing the blade member to the handle.

2. The surgical retractor of claim 1 wherein the lock includes
   a first channel and a second channel, the first channel being disposed within the head member and in communication with the second channel and a first outer surface of the head member, the second channel in communication with the first channel and the aperture of the head member,
   the plunger and a spring housed within the first channel, the spring biasing the plunger toward the first outer surface of the head member, the plunger being of sufficient length to protrude from the head member and having a groove defined by a deep portion and a shallow portion, and
   a first ball and a second ball housed within the second channel, the second ball cooperating with the groove of the plunger to control the extent to which the first ball extends into the aperture of the head member.

3. The surgical retractor of claim 2 wherein the second channel includes an access to the aperture, the access having a width smaller than a diameter of the first ball.

4. The surgical retractor of claim 3 wherein the first and second balls are spherical.

5. The surgical retractor of claim 2 wherein the diameter of the first ball is smaller than a diameter of the second ball.

6. The surgical retractor of claim 5 wherein the first and second balls are spherical.

7. The surgical retractor of claim 2 further including a third channel in communication with the aperture and a second outer surface of the head member and in coaxial alignment with the second channel,
   the second channel having an inner wall that is threaded,
   the retractor further including a screw housing threadably mounted into the second channel and housing the first ball and second ball.

8. The surgical retractor of claim 7 wherein the screw housing has a first end adjacent the aperture, the first end having a width smaller than a diameter of the first ball.

9. The surgical retractor of claim 8 wherein the first and second balls are spherical.

10. The surgical retractor of claim 7 wherein the first and second balls are spherical.

11. The surgical retractor of claim 2 wherein the first and second balls are spherical.

12. The surgical retractor of claim 1 wherein the lock includes
- a first channel and a second channel, the first channel being disposed within the head member and in communication with the second channel and a first outer surface of the head member, the second channel in communication with the first channel and the aperture of the head member,
- the plunger and a spring housed within the first channel, the spring biasing the plunger toward the first outer surface of the head member, the plunger being of sufficient length to protrude from the head member and having a groove defined by a deep portion and a shallow portion, and
- a ball housed within the second channel, the ball cooperating with the groove of the plunger to control the extent to which the ball extends into the aperture of the head member.

13. The surgical retractor of claim 12 wherein the ball is spherical.

14. The surgical retractor of claim 1 wherein the lock includes a channel disposed within the head member and tangential to the aperture and in communication with the aperture and a first outer surface of the head member,
- the plunger and a spring housed within the channel, the spring biasing the plunger toward the first outer surface of the head member, the plunger being of sufficient length to protrude from the head member and having a groove at a point intermediate of the plunger.

15. The surgical retractor of claim 14 wherein the channel traverses the head member and defines a first opening at the first outer surface of the head member and a second opening at a second outer surface of the head member, the first opening including a lip that defines a passage having a first width smaller than a second width of the channel, the second opening including a threaded portion;
- the surgical retractor further including a threaded plug for cooperation with the threaded portion of the second opening;
- the plunger including a first end, a second end, a ridge and a groove, the first end of the plunger having a third width smaller than the first width of the passage of the first opening and a length sufficient to extend through the passage and out of the first opening, the ridge being adjacent the first end and housed within the channel such that the ridge abuts the lip of the first opening to prevent the plunger from passing through the passage, the groove being positioned between the ridge and the second end of the plunger, the groove having a fourth width smaller than a fifth width of the second end, the fifth width of the second end protruding into the aperture when the ridge abuts the lip;
- the spring being disposed between the threaded plug and the plunger.

16. The surgical retractor of claim 15 wherein the plunger is generally cylindrical.

17. A surgical retractor comprising a handle and a blade member, said blade member interlocking with said handle and rotatably mounted thereto, said handle including:
- (i) a head member having an aperture defined by a cylindrical surface; and
- (ii) a lock mechanism, said blade member comprising
- (i) a blade; and
- (ii) a connector secured to said blade and sized for moving within said aperture, said connector having an outer cylindrical surface of a size for bearing against said inner cylindrical surface during rotation of said blade member relative to said handle, said lock mechanism including a first channel and a second channel, the first channel being disposed within the head member and in communication with the second channel and a first outer surface of the head member, the second channel in communication with the first channel and the aperture of the head member, a plunger and a spring housed within the first channel, the spring biasing the plunger toward the first outer surface of the head member, the plunger being of sufficient length to protrude from the head member and having a groove defined by a deep portion and a shallow portion, and a first ball and a second ball housed within the second channel, the second ball cooperating with the groove of the plunger to control the extent to which the first ball extends into the aperture of the head member.

18. The surgical retractor of claim 17 wherein the first and second balls are spherical.

* * * * *